US009529971B2

(12) United States Patent
Huteaux et al.

(10) Patent No.: US 9,529,971 B2
(45) Date of Patent: Dec. 27, 2016

(54) METHOD FOR THE ELECTRONIC AUTHENTICATING OF A HANDWRITTEN SIGNATURE, CORRESPONDING MODULE AND COMPUTER PROGRAM

(75) Inventors: Fabien Huteaux, Boulogne-Billancourt (FR); Alexandre Kroupski, Savigny-sur-Orge (FR)

(73) Assignee: INGENICO GROUP, Paris (FR)

( * ) Notice: Subject to any disclaimer, the term of this patent is extended or adjusted under 35 U.S.C. 154(b) by 798 days.

(21) Appl. No.: 13/348,222

(22) Filed: Jan. 11, 2012

(65) Prior Publication Data

US 2012/0207393 A1 Aug. 16, 2012

(30) Foreign Application Priority Data

Jan. 11, 2011 (FR) ...................................... 11 50236

(51) Int. Cl.
| | | |
|---|---|---|
| *G06K 9/00* | (2006.01) | |
| *G06K 7/00* | (2006.01) | |
| *G06F 19/00* | (2011.01) | |
| *G06K 9/22* | (2006.01) | |

(52) U.S. Cl.
CPC ......... *G06F 19/345* (2013.01); *G06K 9/00174* (2013.01); *G06K 9/224* (2013.01)

(58) Field of Classification Search
USPC ................................................ 382/119, 312
See application file for complete search history.

(56) References Cited

U.S. PATENT DOCUMENTS

| | | | | |
|---|---|---|---|---|
| 3,699,517 A | * | 10/1972 | Dyche ................. | G07C 9/0015 382/122 |
| 4,475,235 A | * | 10/1984 | Graham ............... | G06F 3/0414 178/18.06 |
| 4,878,553 A | | 11/1989 | Yamanami et al. | |
| 5,028,745 A | | 7/1991 | Yamanami et al. | |
| 5,396,443 A | * | 3/1995 | Mese ................... | G06F 1/3215 713/321 |

(Continued)

FOREIGN PATENT DOCUMENTS

| | | |
|---|---|---|
| EP | 0727756 A1 | 8/1996 |
| EP | 0696019 B1 | 10/2000 |

(Continued)

OTHER PUBLICATIONS

Kekre et al., "Gabor Filter Based Feature Vector for Dynamic Signature Recognition", International Journal of Computer Applications, May 1, 2010.

(Continued)

*Primary Examiner* — Kathleen Y Dulaney
(74) *Attorney, Agent, or Firm* — David D. Brush; Westman Champlin & Koehler, P.A.

(57) ABSTRACT

A method and apparatus are provided for electronically authenticating a handwritten signature of a user, entered on a writing surface via a writing instrument. The method includes acquiring, by the writing surface, at least one instant during the entering of the signature, of at least one piece of data representing the altitude z of the writing instrument relative to the writing surface, in an area of proximity to the writing surface; and authenticating the entered handwritten signature by taking account of at least the altitude z.

11 Claims, 2 Drawing Sheets

(56) References Cited

U.S. PATENT DOCUMENTS

| | | | | |
|---|---|---|---|---|
| 5,600,105 | A * | 2/1997 | Fukuzaki | G06F 3/046 178/18.07 |
| 5,682,019 | A * | 10/1997 | Katsurahira | G06F 3/046 178/18.07 |
| 5,774,571 | A * | 6/1998 | Marshall | 382/119 |
| 5,781,661 | A | 7/1998 | Hiraiwa et al. | |
| 5,999,170 | A * | 12/1999 | Ooura | G06F 3/03545 345/173 |
| 6,160,914 | A | 12/2000 | Muroya | |
| 6,417,846 | B1 * | 7/2002 | Lee | G06F 3/03545 178/18.01 |
| 6,486,874 | B1 * | 11/2002 | Muthuswamy | G06F 3/04883 178/18.01 |
| 6,640,007 | B1 * | 10/2003 | Niie | G06K 1/128 340/5.61 |
| 7,239,727 | B2 * | 7/2007 | Taylor | G06K 19/06 382/119 |
| 7,454,042 | B2 * | 11/2008 | Lee | G06K 9/00154 382/119 |
| 8,253,697 | B2 * | 8/2012 | Fleck | G06F 3/0418 178/18.01 |
| 2003/0117378 | A1 * | 6/2003 | Carro | G06F 3/04883 345/173 |
| 2003/0217871 | A1 * | 11/2003 | Chao | G06F 3/046 178/18.01 |
| 2003/0231170 | A1 * | 12/2003 | Yoshikawa | G06F 3/041 345/173 |
| 2005/0105781 | A1 * | 5/2005 | Sakamoto | G06K 9/00154 382/119 |
| 2006/0109252 | A1 * | 5/2006 | Kolmykov-Zotov | G06F 3/03545 345/173 |
| 2006/0159344 | A1 * | 7/2006 | Shao | G06F 3/0346 382/186 |
| 2008/0106520 | A1 * | 5/2008 | Free | G06F 3/03545 345/173 |
| 2009/0033632 | A1 * | 2/2009 | Szolyga | G06F 1/169 345/173 |
| 2011/0267310 | A1 * | 11/2011 | Tsukahara | G06F 3/0416 345/174 |
| 2012/0113056 | A1 * | 5/2012 | Koizumi | H04N 5/232 345/175 |
| 2015/0077374 | A1 * | 3/2015 | Takano | G06F 3/0418 345/173 |

FOREIGN PATENT DOCUMENTS

| | | |
|---|---|---|
| EP | 1846868 B1 | 11/2008 |
| FR | 2842627 A1 | 1/2004 |
| FR | 2842627 B1 | 1/2004 |
| WO | 9812661 A1 | 3/1998 |

OTHER PUBLICATIONS

Bang et al., "Self-Contained Spatial Input Device for Wearable Computer", Wearable Computers, Oct. 21, 2003.

Zhoncheng Wu et al., "The Design of Digital Handwriting Forces Vector Ink and its Application on Online Signature Verification", Intelligent Robots and Systems, Oct. 1, 2006.

Hangai S. et al., "On-Line Signature Verification Based on Altitude and Direction of Pen Movement", Multimedia and Expo, Jul. 30, 2000.

Plamondon et al., "Automatic Signature Verification and Writer Identification—The State of the Art", Pattern Recognition, Mar. 1, 1989.

French Search Report for French Application No. 1105236, dated Aug. 2, 2011.

"How the Wacom cordless, batteryless pen works", Wacom Tech Paper—Intuos4, 2009, available at http://www.wacom.eu/_bib_user/downloads/tech_i4_en.pdf.

"EMR® (Electro-Magnetic Resonance) Technology", Wacom Components, 2007, available at http://www.wacom-components.com/english/technology/emr.html.

* cited by examiner

METHOD FOR THE ELECTRONIC AUTHENTICATING OF A HANDWRITTEN SIGNATURE, CORRESPONDING MODULE AND COMPUTER PROGRAM

CROSS-REFERENCE TO RELATED APPLICATIONS

None.

STATEMENT REGARDING FEDERALLY SPONSORED RESEARCH OR DEVELOPMENT

None.

THE NAMES OF PARTIES TO A JOINT RESEARCH AGREEMENT

None.

FIELD OF THE DISCLOSURE

The field of the disclosure is that of the authenticating of persons, and especially the electronic authenticating of signatures handwritten by persons.

More particularly, the disclosure pertains to the authenticating of a handwritten signature on a writing surface comprising a capacitive touch area.

BACKGROUND OF THE DISCLOSURE

At present, there are a certain number of techniques for authenticating handwritten signatures based essentially on measurements of correlation between characteristics of a signature to be authenticated and preliminarily acquired reference characteristics of authorized persons.

The current authentication techniques can be classified under two major categories: a posteriori authentication (or post-authentication) techniques and "real-time" authentication techniques.

The first category of techniques is based on an analysis of characteristics of the signature entered (the size and/or the shape of the letters for example) on the writing surface on which the signature is entered (embossed features created by the entering of the signature on a paper document for example) after the signature has been entered.

The second category of techniques is based on an analysis of characteristics of the signature obtained as and when the signature is entered (the pressure of the writing instrument on the writing surface and/or acceleration of the writing instrument during the signing operation for example), which can be combined with characteristics of the first category of techniques.

This second category of techniques requires the implementation of technical means during the real-time entering of the signature such as for example the use of an accelerometer on the writing instrument, or a pressure sensor on the writing surface.

One of the most important goals to be achieved for these techniques for authenticating of a handwritten signature pertains to the level of security provided, this level being essentially related to the number of characteristics analyzed.

Indeed, the greater the number of characteristics analyzed, the greater is the reliability of the authentication.

By contrast, the greater the number of characteristics analyzed, the higher are the costs of implementation since the means used to obtain these characteristics as well as the means for processing the obtained characteristics have to be numerous, with a view to subsequent authentication.

Thus, among current techniques, it can be seen that those implemented for "large-scale" consumer products (such as graphic tablets) are based on a fairly restricted number of characteristics, for reasons of cost, whereas those implemented in professional products (such as signature tablets) are based on a fairly large number of characteristics and entail an equally high cost of implementation but a higher level of security.

For example, there are "real-time" authentication techniques based on the analysis of characteristics such as a 2D representation of the signature entered, associated with a parameter representing the pressure of the writing instrument on the writing surface and/or a parameter representing the acceleration of the writing instrument along all three axes of space. These techniques are relatively costly because they call for the use of sensors both on the writing surface and on the writing instrument. Furthermore, they also call for complex operations for processing the different captured pieces of data, so that it is possible to then perform the measurements of correlation and thus authenticate the handwritten signature entered.

One drawback of current techniques for authenticating of a handwritten signature therefore lies in the resolution of the cost/security trade-off, i.e. in the choice of greater complexity for a greater level of security or the converse choice.

Thus, there is a need to propose a technique of electronic authentication of a handwritten signature which can provide a maximum level of security without substantially increasing the complexity or the cost of implementation.

SUMMARY

An exemplary embodiment of the present application is directed to a method for the electronic authenticating of a handwritten signature of a user, entered on a writing surface via a writing instrument.

According to an embodiment of the invention, such a method comprises:
  a step of acquisition, by the writing surface, at one instant at least of the entering of the signature, of at least one piece of data representing the altitude z of the writing instrument relatively to the writing surface, in an area of proximity to the writing surface, said altitude z corresponding to a vertical variable distance separating the writing end of said writing instrument from said writing surface.
  a step of authenticating the entered handwritten signature that takes account of at least the altitude z.

Thus, an embodiment of the invention makes it possible to mitigate the drawbacks of the prior art by the simple and low-cost use of a "real-time" characteristic of a handwritten signature representing the altitude of the writing instrument above the writing surface.

According to an embodiment of the invention, the term "altitude" means the vertical variable distance separating the writing extremity of said writing instrument from said writing surface.

This characteristic can be distinguished from those used in the prior art by the fact that it does not give any binary type of information indicating whether the writing instrument is or is not in contact with the writing surface, but a broader piece of information representing the altitude, or a variation of the altitude, of the writing instrument relatively to the writing surface.

Furthermore, an embodiment of the invention can advantageously be distinguished from the prior-art techniques by the mode of acquisition of the data on altitude. Indeed, according to an embodiment of the invention, this piece of data on altitude is acquired by the writing surface itself without any particular implementation at the level of the writing instrument. Furthermore, this implementation requires few prior settings or no prior settings, and no specific maintenance, unlike in the prior-art techniques that use optical sensors for example.

Thus, the implementation of an embodiment of the invention is simplified in terms of techniques and therefore makes it possible to minimize costs.

Furthermore, according to an embodiment of the invention, the electronic authenticating of the handwritten signature entered by the user takes account especially of the data on altitude acquired by the writing surface, thus reinforcing the level of security of the authenticating. Indeed, this characteristic pertaining to the altitude of the writing instrument forms part of the unique biometric characteristics that can serve to authenticate a user through the authenticating of his handwritten signature.

According to one particular aspect of an embodiment of the invention, the step of acquisition implements a measurement of a capacitance by means of a capacitive touch area of the writing surface.

Thus, an embodiment of the invention is implemented in a device comprising a writing surface having at least one capacitive touch area enabling the acquisition of the data on altitude when a user enters his signature.

Indeed, through current or future capacitive touch technologies, an embodiment of the invention can exploit an additional characteristic of the detection of the writing instrument on a writing surface of this type, representing the altitude of the writing instrument relatively to the writing surface, such characteristic being distinct of the coordinates (x,y) that can be obtained by classic means.

According to one particular embodiment of the invention, the acquisition step furthermore delivers at least two other pieces of data representing the localization of the writing instrument in a plane formed by the writing surface, denoted as pieces of data x and y.

Thus, according to this embodiment of the invention, the authenticating of a signature is based on several other characteristics, in addition to the data on altitude, thus reinforcing the level of security.

For example, the coordinates (x,y,z) of the writing instrument are acquired, enabling a precise localization of the writing instrument on and above the writing surface.

In particular, the pieces of data x, y and z represent the localization of the writing end of the writing instrument, i.e. the end that is in contact with or close to the writing surface (for example the tip of a stylus).

According to one particular aspect of an embodiment of the invention, the method comprises a step for processing at least one of the pieces of data acquired during the acquisition step, comprising at least one of the following sub-steps:
  filtering;
  linearization;
  interpolation;
  standardization;
  thresholding.

Thus, according to this embodiment, the invention, as the case may be, provides for the performance of a mathematical processing operation on one of the pieces of data acquired, especially the data on altitude. Indeed, the acquisition of this piece of data may be imprecise or may have deteriorated because it can be the case that there is no contact between the writing surface and the writing instrument. Thus, an acquired piece of data on altitude may for example be "normalized" after acquisition so that it can be used thereafter to authenticate the handwritten signature.

In particular, the piece of data on altitude z belongs to the group comprising:
  a piece of data representing a measurement of the altitude of the writing instrument with respect to the writing surface;
  a piece of data representing a variation between two measurements of the altitude of the writing instrument with respect to the writing surface.

Thus, an embodiment of the invention makes it possible to acquire not only a piece of data representing the altitude of the writing instrument, but also a piece of data representing a changing, or a difference, of altitude of the writing instrument, as and when the signature is entered. Thus, an embodiment of the invention makes it possible to know the progress of the altitude of the writing instrument as a function of time, thus reinforcing the level of security.

According to one particular embodiment of the invention, the acquisition step comprises a substep for obtaining a data representing the altitude z of the writing instrument, which is implemented periodically during the entering of the handwritten signature, delivering a set of data representing the course of the writing instrument above the writing surface as a function of time.

Thus, a plurality of pieces of data on altitude can be acquired as and when the signature is entered by the user, thus making it possible to obtain a set of pieces of data representing the course of the writing instrument above the writing surface as a function of time.

Besides, according to another aspect of an embodiment of the invention, the acquisition step comprises a sub-step for determining a speed and/or an acceleration of the writing instrument.

Indeed, a piece of information such as this on speed and/or acceleration represents the specificity of a signature of a given user, and can therefore also reinforce the level of security of the authenticating.

According to another embodiment of the invention, the invention comprises a preliminary learning phase comprising the following steps:
  the entering, on a writing surface via a writing instrument, of at least one handwritten signature called a reference signature coming from an authorized user;
  the acquisition, by the writing surface, at one instant at least of the entering of the signature, of at least one piece of data representing the altitude z of the writing instrument relatively to the writing surface, in an area of proximity to the writing surface, denoted as a piece of reference altitude data;
  the storage of the piece of reference altitude data.

Thus, the method provides for a learning phase, enabling the listing of all the users authorized, with their associated signature, serving subsequently as a reference for the authenticating.

These reference signatures can for example be stored in an authenticating server at a distance from a device subsequently used for the real-time entering and authenticating of a signature. In this case, at the time of the authenticating of the signature entered on the authenticating device, this device interrogates the authenticating server in order to have access to the reference signatures.

The reference signatures may also be stored in the device itself, then used for the entering and authenticating in real time of a signature.

In particular, the step for authenticating the handwritten signature includes a sub-step for measuring the correlation between at least one piece of data on altitude z acquired during the acquisition step and at least one piece of reference altitude data.

An embodiment of the invention also pertains to a module for the electronic authenticating of a user's handwritten signature, entered on a writing surface through a writing instrument, implementing:

means of acquisition, by the writing surface, at one instant at least of the entering of the signature, of at least one piece of data representing the altitude z of the writing instrument relatively to the writing surface in an area of proximity to the writing surface), said altitude z corresponding to a vertical variable distance separating a writing end of said writing instrument from said writing surface;

means for authenticating the handwritten signature taking account of at least the altitude z.

An authenticating module of this kind can especially form part of an electronic payment terminal, a PDA or a portable telephone.

Finally, an embodiment of the invention pertains to a computer program stored on a non-transitory computer-readable medium and comprising instructions to execute the steps of the authenticating method as described here above, when the program is executed by a computer.

BRIEF DESCRIPTION OF THE DRAWINGS

Other features and advantages shall appear more clearly from the following description of a particular embodiment, given by way of a simple, illustrative and non-restrictive example and from the appended drawings, of which.

DETAILED DESCRIPTION OF ILLUSTRATIVE EMBODIMENTS

1. General Principle

The general principle of an embodiment of the invention relies on the acquisition, in real time and by the writing surface itself, of at least one piece of data representing the altitude of a writing instrument during the entering of a user's handwritten signature, enabling the reinforcement of the level of security of an authenticating of a handwritten signature based on the acquired piece of altitude data, while at the same time minimizing costs of implementation.

Indeed, since the piece of altitude is acquired by the writing surface itself, an embodiment of the invention does not require any particular implementation of the writing instrument, and requires few settings or no settings and no special maintenance, unlike for example in the use of the specific optical sensors of certain prior-art techniques.

Furthermore, the altitude data acquired may be associated with a certain number of other characteristics of signatures acquired in real time in order to reinforce the security level of the authenticating of the signature. Indeed, this characteristic pertaining to the altitude of the writing instrument forms part of the unique biometric characteristics that can serve to authenticate a user through the authenticating of his or her handwritten signature.

2. Description of One Embodiment

Figure 1A:
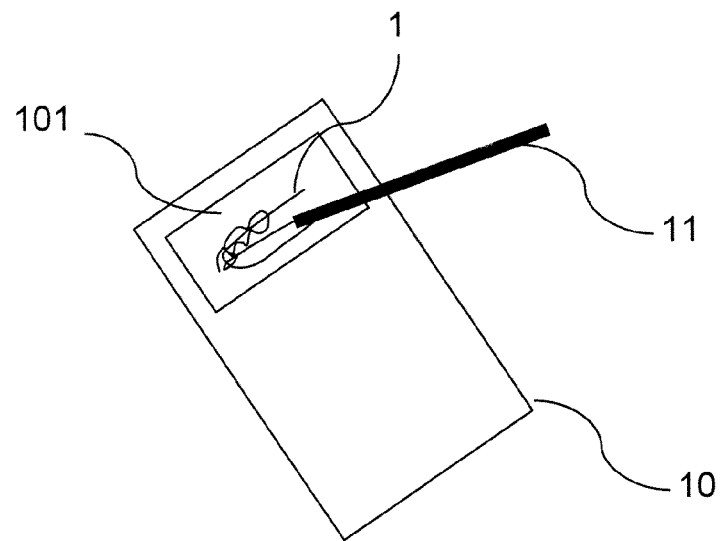
FIGS. 1A and 1B respectively illustrate an example of a system implementing the method for the electronic authenticating of a handwritten signature and the main steps of this method for authenticating, according to one embodiment of the invention.
Figure 1B:
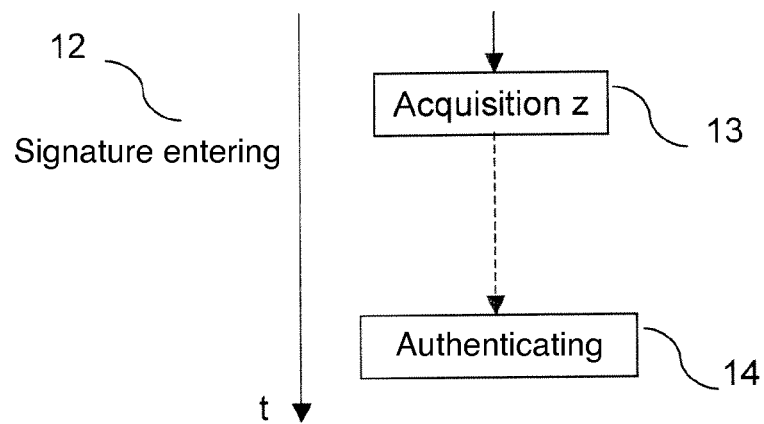

Referring now to FIGS. 1A and 1B, we present an example of a system for implementing an embodiment of the invention and the main steps of the method for authenticating implemented in such a system according to an embodiment of the invention.

As illustrated in FIG. 1A, we consider an authenticating module 10 having a writing surface 101 comprising a capacitive touch area on which the user enters his signature 1 for authenticating.

For example, the authenticating module is integrated into a payment terminal, a mobile telephone, a PDA etc.

The signature 1 is entered through a writing instrument 11 adapted to an entering on the capacitive touch area, for example a stylus.

FIG. 1B presents the main steps of the method for authenticating a handwritten signature implemented in a system as described here above with reference to FIG. 1A.

A step 13 for acquiring a piece of data z on altitude of the writing instrument is implemented, at one instant at least of the step 12 for entering the handwritten signature, and advantageously at a plurality of instants during the entering of the signature.

For example, it is possible to acquire three hundreds samples per second during the entering of the signature to obtain efficient performance in terms of reliability of authentication.

Besides, depending on the type of capacitive touch area, it is possible to acquire pieces of data on altitude of up to two centimeters above the writing surface.

According to one advantageous variant of this embodiment, the step of acquisition enables the acquisition of a plurality of other pieces of data on the position of the writing instrument relatively to the capacitive touch area of the writing surface, such as the coordinates (x,y) of the writing instrument on the writing surface, at several instants of the signing operation. Pieces of data on pressure on the writing surface can also be acquired. This variant makes it possible to reinforce the authentication by providing a greater number of "real-time" characteristics of the signature.

It must be noted that the coordinates x, y and z are acquired by the capacitive touch area of the writing surface itself, without calling for any particular implementation of the writing instrument. Besides, this implementation by the writing surface itself does not require any settings either, or few settings, nor does it require any particular maintenance, unlike in the use of optical sensors on the writing instrument for example.

After the acquisition step 13, or as and when the pieces of data on altitude z are acquired, an authenticating step 14 is implemented delivering a result, which may be positive or negative, of authentication of the user who entered the signature.

According to a first variant, the authenticating step 14 can be implemented after the entering of the signature and therefore after the acquisition of all the data on altitude. This variant is for example implemented when the pieces of reference data used for the authentication are available on a remote server, with which a communications link has to be initiated to enable the use of these pieces of reference data.

According to another variant, the authentication can be implemented as soon as a predetermined number of pieces of data is acquired, so as to enable fast authentication. For example, this variant is implemented when the pieces of reference data are available on the signature entering module itself, thus not necessitating any communication with a remote server.

According to this embodiment, the authenticating step 14 implements a correlation between the acquired data (altitude data z and possibly other pieces of data described here above) during the entering of the signature, and the available pieces of reference data, listed for a certain number of authorized users during a learning phase.

For example, an embodiment of the invention uses known correlation techniques, not described here, extended to the correlation of altitude data acquired according to an embodiment of the invention. Thus, there are correlation techniques based on a set of data (x, y, p, t) representing the (x,y) coordinates of the writing instrument and the pressure on the writing surface as a function of time. According to one variant, it is therefore possible to extend these correlation techniques to a set of data (x, y, z, t) or a set of data (x, y, z, p, t) for even greater security.

Figure 2A:
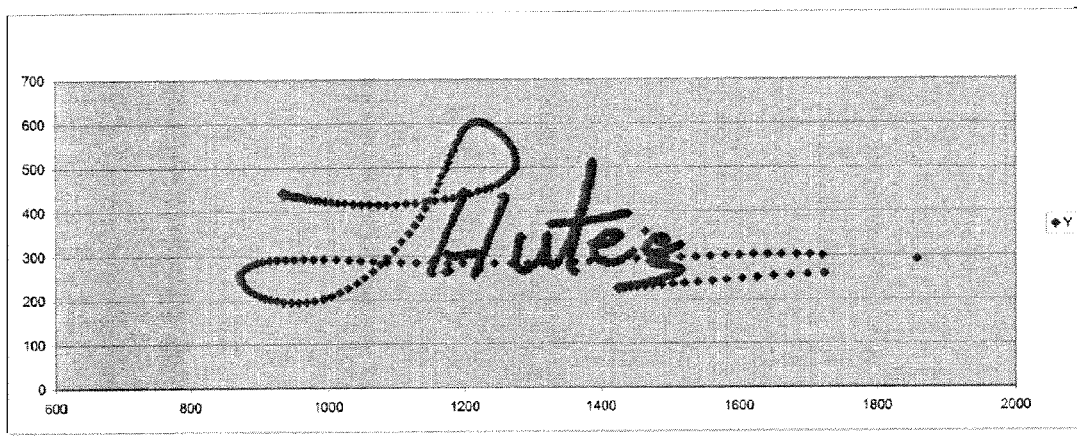
FIGS. 2A and 2B respectively illustrate an example of a signature entered in a system according to FIG. 1A and an example of pieces of altitude data z acquired according to one embodiment of the method for authenticating of the invention.
Figure 2B:
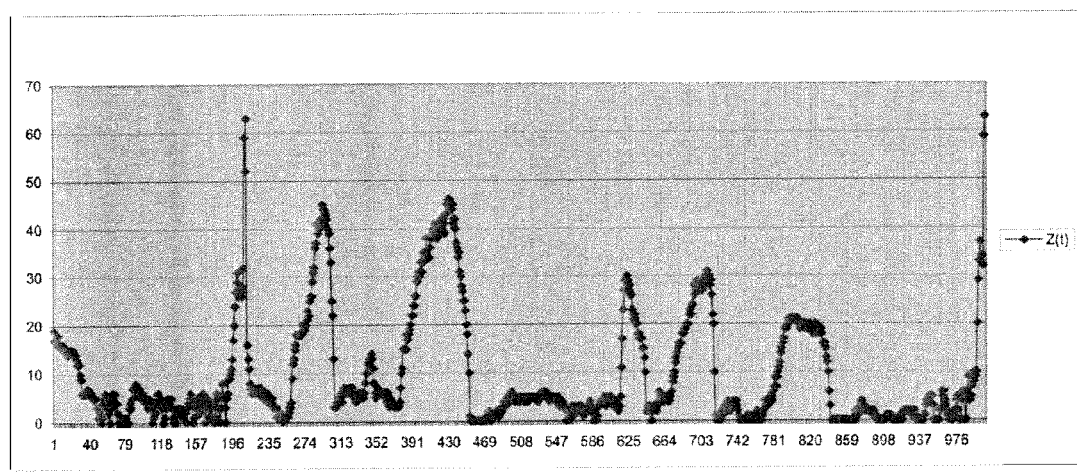

Referring now to FIGS. 2A and 2B, we describe respectively an example of an entered signature of this kind as well as a representation, as a function of time, of a plurality of data on altitude z acquired during the entering of the signature.

According to variants of this embodiment, especially related to the type of capacitive touch area used as a writing surface, the data on altitude z acquired during the entering of the signature can be processed before being used to authenticate the user.

For example, according to a first variant, the acquired pieces of data on altitude z are normalized according to predetermined criteria, pertaining to the type of capacitive touch area. In this way, the pieces of normalized altitude data can then be used during the authenticating of the signature, even if the pieces of reference altitude data have not been acquired with a device having the same type of capacitive touch area. This variant ensures compatibility of authentication whatever the signature entering device.

According to another variant, a space is defined above the capacitive touch area, that is linear and contiguous and used for measuring altitude data, taking account of defects, if any, of acquisition of the pieces of altitude data. This variant thus makes it possible to obtain reliable and usable pieces of altitude data, taking account of imprecision if any in acquisition.

FIG. 2B illustrates an example of a plurality of pieces of altitude data acquired during the entering of the signature illustrated in FIG. 2A. These pieces of altitude data can be exploited for an authentication of a handwritten signature, i.e. they are capable of being correlated with a plurality of reference altitude data preliminarily acquired during a learning phase.

According to yet another variant of this embodiment, compatible with previously described variants, the pieces of altitude data acquired are processed so as to obtain a representation of the change of the altitude of the writing instrument as and when the signature is written. Thus, pieces of data relative to the altitude of the writing instrument are obtained, and are then correlated with pieces of data pertaining to the reference altitude. This variant makes it possible to take account more efficiently of the overall change of the altitude of the writing instrument during the entering of the signature.

Although the present disclosure has been described with reference to one or more examples, workers skilled in the art will recognize that changes may be made in form and detail without departing from the scope of the disclosure and/or the appended claims.

The invention claimed is:

1. A method for electronic authenticating a handwritten signature of a user entered on a writing surface via a writing instrument, wherein the method comprises:
   acquiring, by a capacitive touch area of said writing surface, periodically during an entering of said signature, altitude data consisting of an altitude z of said writing instrument relative to said writing surface, in an area of proximity to said writing surface, delivering a set of the altitude data representing a course of said writing instrument above said writing surface as a function of time as the writing instrument moves across the capacitive touch area, said set of the altitude data corresponding to a vertical variable distance separating a writing end of said writing instrument from said writing surface, said acquiring of the altitude data implementing a measurement of a capacitance by the capacitive touch area of said writing surface; and
   authenticating said entered handwritten signature by determining said entered handwritten signature correlates to a reference signature by only correlating the set of the altitude data with reference altitude data of the reference signature.

2. The method for authenticating according to claim 1, wherein said acquiring furthermore delivers at least two other pieces of data representing localization of said writing instrument in a plane formed by said writing surface, denoted as pieces of data x and y.

3. The method for authenticating according to claim 2, wherein said pieces of data x, y and z represent the localization of the writing end of said writing instrument.

4. The method for authenticating according to claim 1, wherein the method comprises processing said altitude data, comprising at least one of the following:
   filtering;
   linearization;
   interpolation;
   standardization;
   thresholding.

5. The method for authenticating according to claim 1, wherein said altitude data belongs to the group consisting of:
   data representing a measurement of the altitude of said writing instrument with respect to said writing surface;
   data representing a variation between two measurements of the altitude of said writing instrument with respect to said writing surface.

6. The method for authenticating according to claim 5, wherein said acquiring comprises determining a speed and/or an acceleration of said writing instrument.

7. The method for authenticating according to claim 1, wherein the method comprises a preliminary learning phase comprising:
   a preliminary entering, on said writing surface through said writing instrument, at least one handwritten signature called the reference signature coming from an authorized user;
   a preliminary acquisition, by said writing surface, at at least one instant during said preliminary entering of said reference signature, of at least one piece of data representing a reference altitude z of said writing instrument relative to said writing surface, in an area of proximity to said writing surface, denoted as a piece of the reference altitude data;

storage of said at least one piece of reference altitude data.

8. The method or electronic authenticating according to claim 7, wherein said authenticating said handwritten signature comprises measuring correlation between said altitude data representing an altitude z acquired during said acquiring and said piece of reference altitude data.

9. The method for authenticating according to claim 1, wherein said acquiring comprises determining a speed and/or an acceleration of said writing instrument.

10. A device configured to form part of an electronic payment terminal for electronic authenticating a handwritten signature of a user, entered on a writing surface via a writing instrument, wherein the module comprises:

means for acquiring, by a capacitive touch area of said writing surface, periodically during an entering of said signature, altitude data consisting of an altitude z of said writing instrument relative to said writing surface in an area of proximity to said writing surface, delivering a set of the altitude data representing a course of said writing instrument above said writing surface as a function of time as the writing instrument moves across the capacitive touch area, said set of the altitude data corresponding to a vertical variable distance separating a writing end of said writing instrument from said writing surface, said means for acquiring the altitude data implementing a measurement of a capacitance by the capacitive touch area of said writing surface; and means for authenticating said handwritten signature by determining said entered handwritten signature correlates to a reference signature by only correlating the set of the altitude data with reference altitude data of the reference signature.

11. A computer program stored on a non-transitory computer-readable medium and comprising instructions to execute a method of electronically authenticating a handwritten signature of a user entered on a writing surface via a writing instrument, when said program is executed by a computer, wherein the method comprises:

acquiring, by a capacitive touch area of said writing surface, periodically during an entering of said signature, altitude data consisting of an altitude z of said writing instrument relative to said writing surface, in an area of proximity to said writing surface, delivering a set of the altitude data representing a course of said writing instrument above said writing surface as a function of time as the writing instrument moves across the capacitive touch area, said set of the altitude data corresponding to a vertical variable distance separating a writing end of said writing instrument from said writing surface, said acquiring of the altitude data implementing a measurement of a capacitance by the capacitive touch area of said writing surface; and authenticating said entered handwritten signature by determining said entered handwritten signature correlates to a reference signature by only correlating the set of the altitude data with reference altitude data of the reference signature.

* * * * *